United States Patent [19]

Quesenberry et al.

[11] Patent Number: 5,583,199
[45] Date of Patent: Dec. 10, 1996

[54] HEMOPOIETIC GROWTH-REGULATORY CALMODULIN-BINDING PROTEIN AND METHODS OF USING THE SAME

[75] Inventors: Peter J. Quesenberry; G. Prem-Veer Reddy, both of Charlottesville, Va.

[73] Assignee: University of Virginia Patents Foundation, Charlottesville, Va.

[21] Appl. No.: 154,722

[22] Filed: Nov. 19, 1993

Related U.S. Application Data

[63] Continuation of Ser. No. 791,400, Nov. 14, 1991, abandoned.

[51] Int. Cl.⁶ .......................... C07K 2/00; C07K 14/475
[52] U.S. Cl. .......................... 530/350; 530/358; 530/412; 530/829
[58] Field of Search ...................... 530/350, 358, 530/387.9, 412, 827, 829; 514/2

[56] References Cited

PUBLICATIONS

H. Hirling et al. Nature 339:562–564 Jun. 15, 1989.
C. Subramangam et al. J. Cell. Physiol. 144:423–428 1990.
G. Prem Veer Reddy et al. Blood 79(8):1946–1955 Apr. 15, 1992.
Q. P. Cao et al., Biochemistry 34:3878, 1995.

*Primary Examiner*—Stephen G. Walsh
*Assistant Examiner*—Lorraine Spector
*Attorney, Agent, or Firm*—Oblon, Spivak, McClelland, Maier & Neustadt, P.C.

[57] ABSTRACT

A 68 kDa a calmodulin-binding protein obtained from cytoplasmic or nuclear eukaryotic cell fractions, which is induced in hemopoietic factor-dependent cell lines by at least one of the following cytokines: granulocyte-macrophage colony stimulating factor, granulocyte colony stimulating factor, interleukin-3 or interleukin-6.

17 Claims, 12 Drawing Sheets

HEMOPOIETIC GROWTH-REGULATORY CALMODULIN-BINDING PROTEIN AND METHODS OF USING THE SAME

This invention was made with U.S. government support under AI 23869 grant awarded by the National Institutes of Health, and the government may, therefore, have certain rights in the same.

This application is a Continuation of application Ser. No. 07/791,400, filed on Nov. 14, 1991, now abandoned.

BACKGROUND OF THE INVENTION

1. Field of the Invention

The present invention relates to a hemopoietic growth-regulatory calmodulin-binding protein and methods of using the same in the management of both non-malignant and malignant hematological diseases.

2. Description of the Background

Proliferation of eukaryotic cells is controlled by a series of regulatory events, including expression and intracellular redistribution of enzymes and other proteins associated with DNA synthesis, occurring during G1 phase of the cell cycle. Although it is well known that growth factors or cytokines are required to stimulate the proliferation of hemopoietic cells, very little is known about the regulatory process(es) stemming from growth factor/receptor interactions on the membrane that culminates in the induction of nuclear DNA replication and cellular proliferation.

Calmodulin (CAM) and other members of the family of calcium-modulated proteins are major eukaryotic intracellular receptors for the element calcium, a substance of major importance in the regulation of many diverse cell processes such as motility, proliferation and nutrient utilization.

Calmodulin is ubiquitously distributed in eukaryotic cells and has been isolated from bovine brain, rat testis and marine invertebrates. The protein is a relatively small, acidic, stable protein having a molecular weight of 15,000 to 19,000 lacking cysteine, hydroxyproline and tryptophan. Moreover, it has a high content of acidic amino acids and low tyrosine content and almost all calmodulins isolated contain a single, fully trimethylated lysyl residue.

Further, calmodulins obtained from a wide variety of phylogenetically different sources are similar in amino acid sequence and in physico-chemical and biological properties. Hence, the protein lacks both species and tissue specificity and appears to be structurally and functionally conserved throughout evolution.

Progression of eukaryotic cells from G1 to S phase is also known to be highly dependent on events regulated by calcium, which is known to exert its effects either by controlling $Ca^{2+}$-sensitive, phospholipid-dependent protein kinase C, or activating the $Ca^{2+}$-binding protein, CaM. Both of these pathways are induced by the interaction of extracellular growth factors with their membrane receptors which stimulate a membrane-bound enzyme, phospholipase C. Phospholipase C catalyzes the conversion of phosphatidylinositol 4,5-bisphosphate to diacylglycerol or to inositol 1,4,5-triphosphate. Diacylglycerol activates phosphatidyl serine-dependent protein kinase C which phosphorylates serine and/or threonine residues of its target proteins. Inositol 1,4,5-triphosphate is believed to release $Ca^{2+}$ from the endoplasmic reticulum stores, leading to the activation of CaM. Activated CaM regulates cellular cyclic nucleotides by activating phosphodiesterase, adenylate cyclase and guanylate cyclase, and protein phosphorylation through activation of CaM-dependent protein kinases and phosphatases. At present, the involvement of protein kinase C and cyclic nucleotides in cellular proliferation is unclear. Further, the role of CaM, activated by inositol 1,4,5-triphosphate-dependent release of $Ca^{2+}$, also remains obscure Inositol 1,4,5-triphosphate is known to stimulate initiation of DNA synthesis by releasing $Ca^{2+}$ from intracellular stores and $Ca^{2+}$ channels are known to be involved in signal transduction of hemopoietic growth factors. By lowering $Ca^{2+}$ levels in cellular medium at the late-prereplicative period (G1/S boundary) of mammalian cells, it appears possible to prevent cells from initiating DNA synthesis by stopping the expression and/or activation of ribonucleotide reductase, and the synthesis of four deoxynucleotides. Further, $Ca^{2+}$-deprived cells appear to undergo dismantling of prereplicative structure and enter a state of quiescence.

Since most of the effects of $Ca^{2+}$ are known to be mediated by the activation of CaM, changes in intracellular CaM levels can also govern $Ca^{2+}$-mediated events. In fact, the integrated role of $Ca^{2+}$ and cellular proliferation is strongly implicated from the following observations: a) CaM levels are elevated 2 to 3 fold at the G1/S boundary; b) there is a complete coincidence between temporal increase in CaM levels and the progression of cells into S phase, regardless of the length of G1; c) there is a direct correlation between intracellular CaM levels and the ability of cells to replicate DNA; d) CaM can stimulate DNA replication in isolated liver cells; e) nuclear CaM undergoes rearrangement during proliferative activation of liver cells; f) progression of cells from G1 to S phase is sensitive to CaM antagonists; and g) the stimulatory effect of $Ca^{2+}$ on DNA synthesis in rat hepatocytes is mimicked by the addition of CaM and is blocked by CaM antagonists and anti-CaM antibody. Thus, CaM, in serving as a $Ca^{2+}$ receptor, appears to play a critical role in the control of cell proliferation.

However, while the interaction between hemopoietic growth factors and their cognate receptors is known to be the primary event in hemopoiesis, the molecular events in proliferative signal transduction following ligand-receptor interaction are not clear. Moreover, at present, there is no known means by which CaM activity can be controlled in order to control the onset of DNA synthesis. It would be extremely desirable, however, if such a means could be found for controlling the progression of cells from G1 into S phase of the cell cycle. Such a means would make it possible to manage both non-malignant and malignant hematological diseases.

SUMMARY OF THE INVENTION

Accordingly, it is an object of the present invention to provide a 68 kDa calmodulin-binding protein (CaM-BP), the appearance of which corresponds with the progression of eukaryotic cells from G1 into S phase of the cell cycle.

It is also an object of the present invention to provide cDNA corresponding to this protein.

It is, moreover, also an object of the present invention to provide monoclonal and polyclonal antibodies to the protein and antisense constructs therefor.

Further, it is also an object of the present invention to provide a method for managing both non-malignant and malignant hematological diseases.

Moreover, it is also an object of the present invention to provide a method for controlling the progression of cells from G1 into S phase of the cell cycle.

BRIEF DESCRIPTION OF THE DRAWINGS

FIGS. 3A–3C illustrate the effect of individual growth factors on intracellular distribution of CaM-BPs in factor-dependent hemopoietic cells.

FIG. 3A illustrates the effect of IL-3 and GM3-CSF on the restoration of nuclear 68 kDa CaM-BP FDC-P1 and 32D cells deprived of WEHI-3 cm.

FIG. 3B illustrates the restoration of nuclear localization of the 68 kDa CaM-BP by exposure to IL-3 G-CSF in NFS-60 cells deprived of WEHI-3 cm.

FIG. 3C illustrates the effect of IL-6 on restoration of 68 kDa CaM-BP in growth factor deprived T1165 cells.

FIG. 5A illustrates $^3$H-thymidine incorporation in acid-precipitable material of FDC-P1 cells at regular intervals after releasing from isoleucine block.

FIG. 5B illustrates thymidine kinase activity in cell lysates of FDC-P1 cells prepared at regular intervals after releasing from isoleucine block.

FIG. 6A illustrates the effect of WEHI-3 cm on the cytoplasmic 68 kDa CaM-BP as the cells progress from G1 to S phase.

FIG. 6B illustrates the effect of WEHI-3 cm on the nuclear 68 kDa CaM-BP as the cells progress from G1 to S phase.

FIG. 6C illustrates changes in nuclear 68 kDa CaM-BP following the release of FDC-P1 cells from isoleucine block under the presence of WEHI-3 cm as determined by densometric analysis of 68 kDa bands on nitrocellulose filters shown in FIG. 6C.

FIG. 6D illustrates the effect of IL-3 and WEHI-3 cm on nuclear localization of the 68 kDa CaM-BP as the cells progress from G1 to S phase.

DETAILED DESCRIPTION OF THE PREFERRED EMBODIMENTS

Figure 1:
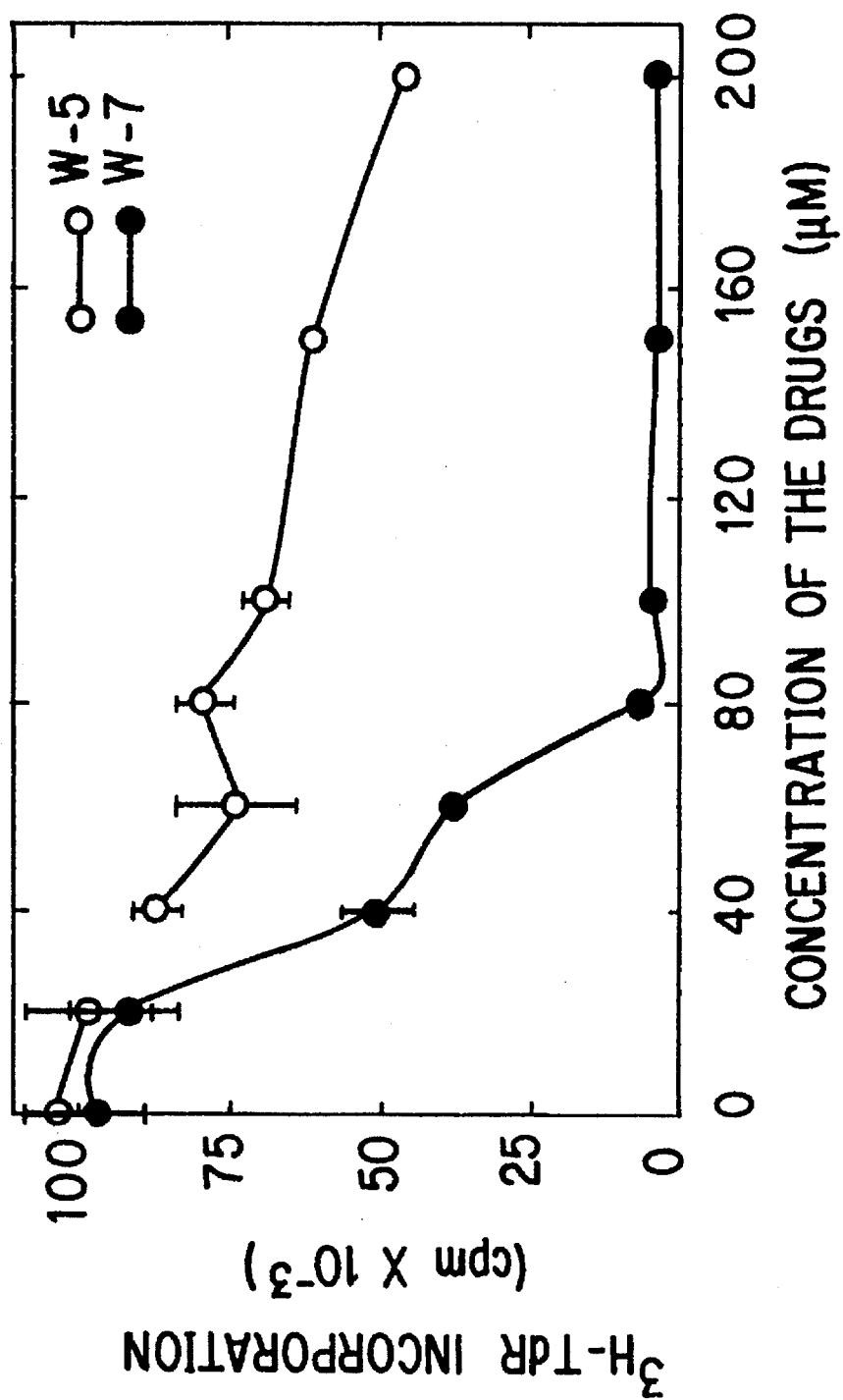
FIG. 1 illustrates the effect of CaM antagonists, W-7 and W-5, on $^3$H-thymidine incorporation into DNA of FDC-P1 cells.

In accordance with the present invention, a 68 kDa calmodulin-binding protein, which is both cytoplasmic and nuclear, has been discovered which is induced in hemopoietic factor-dependent cell lines by granulocyte-macrophage colony stimulating factor (GM-CSF), granulocyte-CSF (G-CSF), interleukin-6 (IL-6) and interleukin-3 (IL-3). Quite surprisingly, the appearance of this protein has also been discovered to correspond with the progression of cells from late G1 into S phase of the cell cycle.

Furthermore, in accordance with the present invention, it has been discovered that the calmodulin-binding protein of the present invention is required for the onset of DNA replication and, therefore, for cell proliferation. It has also been surprisingly discovered that the modulation and the nuclear localization of this specific CaM-BP is dependent on the exposure of hemopoietic cells to cytokines such as IL-3, IL-6 and GM-CSF with proliferative potential and that the nuclear localization of this protein generally coincides directly with the ability of cells to progress from G1 to S phase.

Generally, the 68 kDa protein of the present invention may be obtained from hematopoietic factor dependent cell lines, such as FDC-P1 cells. In general, calmodulin-binding proteins may be separated from either cytoplasmic or nuclear cell fractions by gel electrophoresis under denaturing conditions using the Laemmli procedure. Proteins resolved on the gels are then transferred to nitrocellulose filters using a transphor electrophoresis unit. CaM-BPs on the filters may be identified by employing biotinylated-CaM and alkaline phosphatase conjugated avidin using the procedure of Billingsley et al. Notably, the binding specificity of CaM to the proteins transferred to the nitrocellulose filters is determined by its dependence on $Ca^{+2}$ and by its sensitivity to CaM antagonist W-7. Prestained molecular weight markers may be used to identify relative molecular weights of CaM-BPs detected on the filters.

The present invention is predicated upon the surprising discovery that hemopoietic factor dependent cell lines, such as FDC-P1, 32D, NFS-60 and T 1165, essentially cease to proliferate when deprived of cytokines for about 16–18 hours, even in the presence of fetal calf serum, and that concomitant to the cessation of proliferation, a dramatic depletion of a 68 kDa CaM-BP occurs in both cytoplasmic and nuclear cell fractions. However, within about 6–12 hours of re-exposure to specific cytokines, a restoration of both the nuclear and cytoplasmic 68 kDa CaM-BP was observed.

Furthermore, it was observed that induction and nuclear localization of the 68 kDa CaM-BP by the cytokines coincided temporally with the progression of synchronized FDC-P1 cells from G1 to S phase. By contrast, CSF-1 dependent bone marrow macrophages and BAC-1 cells did not exhibit 68 kDa CaM-BP in the nuclear or cytoplasmic fractions. Thus, it appears that a common mechanism involving nuclear localization of a specific 68 kDa CaM-BP governs the signal transduction pathways of the hemopoietic growth factors Il-3, IL-6, G-CSF and GM-CSF, where receptors are members of the hemopoietin receptor family, and CSF-1 signal transduction appears to involve 68 kDa CaM-BP-independent pathways in inducing cellular proliferation.

Thus, in one aspect, the present invention provides a 68 kDa calmodulin-binding protein, the appearance of which corresponds with the progression of eukaryotic cells from G1 into S phase of the cell cycle.

This protein responds to elimination of WEHI-3 conditioned medium (cm) in a culture medium by exhibiting a decrease therefor in both cytoplasmic and nuclear cell fractions. However, upon re-exposure of the cells to WEHI-3 cm, an almost complete restoration of levels of the 68 kDa CaM-BP in whole cell lysate is observed. Also, the presence of the 68 kDa protein is necessary for cell proliferation.

The 68 kDa CaM-BP of the present invention can also be restored in the nuclear fraction of FDC-P1 cells by the presence of the cytokines IL-3, IL-6, G-CSF and GM-CSF.

The present invention also provides cDNA corresponding to the 68 kDa CaM-BP, monoclonal and polyclonal antibodies to the protein and antisense constructs therefor.

Furthermore, the present invention also provides a method for controlling the progression of cells from G1 into S phase of the cell cycle, and, therefore, a method for managing both malignant and non-malignant diseases.

In general, since the 68 kDa CaM-BP of the present invention is necessary for the progression of cells from G1 to S phase, the inactivation of this protein or blocking its production with either polyclonal or monoclonal antibodies or antisense or both provides a means by which cell progression, and therefore proliferation, can be controlled.

In accordance with the present invention, cell proliferation of any eukaryotic cells may be controlled using the present invention. For example, this method may be used to inhibit cell proliferation in a mammal of malignant eukaryotic cells by interrupting progression of cells from G1 to S phase by administering to the mammal an amount of monoclonal or polyclonal antibodies or antisense or both effective for interrupting progression of cells from G1 to S phase, the antibodies being raised against a 68 kDa calmodulin-binding protein obtained from cytoplasmic or nuclear eukaryotic cells fractions, which is induced in hemopoietic factor-dependent cell lines by at least one of the following cytokines: granulocyte-macrophage colony stimulating factor, granulocyte colony stimulating factor, interleukin-3 and interleukin-6.

Generally, as used herein the term "malignant eukaryotic cells" is defined as and refers to any type of cancer.

The term "cancer" as used herein may be virtually any type of cancer, such as lung cancer, gastrointestinal cancer, melanomas of the skin, prostate cancer, bladder cancer, kidney cancer, brain cancer, breast cancer, ovarian cancer, uterine cancer, cancer of the testes and any of the various lymphomas, including Hodgkin's disease.

The present invention also may be used to inhibit cell proliferation in a mammal of non-malignant eukaryotic cells by interrupting progression of cells from G1 to S phase by administering to the mammal an amount of monoclonal or polyclonal antibodies or both effective for interrupting progression of cells from G1 to S phase, the antibodies being raised against a 68 kDa calmodulin-binding protein obtained from cytoplasmic or nuclear eukaryotic cell fractions, which is induced in hemopoietic factor-dependent cell lines by at least one of the following cytokines: granulocyte-macrophage colony stimulating factor, granulocyte colongy stimulating factor, interleukin-3 and interleukin-6.

Generally, as used herein the term "non-malignant eukaryotic cells" is defined as and refers to any non-cancerous eukaryotic cells. Such cells may either be normal eukaryotic cells or eukaryotic cells exhibiting a diseased condition, such as atherosclerosis.

In order to further illustrate the present invention, reference will now be made to certain examples which are provided solely for illustration and are not intended to be limitative.

Cell lines and their cultures. FDC-P1 (obtained from Dr. Jim Ihle) and 32D (obtained from Dr. Joel Greenberger) cells were maintained routinely in RPMI 1640 (Gibco, Grand Island, N.Y.) supplemented with 10% fetal calf serum (FCS), and 25% WEHI-3 cell conditioned medium (WEHI-3 cm); NFS-60 (obtained from Dr. Donna Rennick) in RPMI 1640 supplemented with 5% FCS, 10% WEHI-3 cm and 50 μM mercaptoethanol; IL-6-dependent tumor induced mouse plasmacytoma T1165 cells (courtesy of Dr. David Bodine) in RPMI 1640 containing 10% FCS, 5% COS cell cm (a source of IL-6), and 50 μM mercaptoethanol; and CSF-1-dependent BAC-1 cells (received from Dr. Ian McNiece, Amgen, Inc.) in Dulbecco's modified Eagle's medium (DMEM) with high glucose (purchased from Whittaker, Walkersville, Md.) supplemented with 15% FCS, 10% NCTC (from MA Bioproducts, Baltimore, Md.), 2 mM glutamine, and 20% L-cell cm (a source of CSF-1). All these culture media contained 100 units/ml penicillin and 100 μg/ml streptomycin and the cultures were maintained at 37° C. in humidified 5% $CO_2$ containing incubators.

Bone marrow macrophage (BMM) isolation and culture. BMM were purified from bone marrow cells obtained from femora and tibia of mice according to the procedure of Gilbert and Stanley. Purified BMM were then grown in DMEM (Gibco, Grand Island, N.Y.) supplemented with 15% FCS, 0.02 mg/ml L-asparagine, 50 μM mercaptoethanol, 100 units/ml penicillin, 100 μg/ml streptomycin and 5% adherent stromal cell line TC-1 conditioned medium (a source of CSF-1) at 37° C. in a humidified incubator containing 10% $CO_2$.

Measurement of $^3$H-thymidine incorporation into DNA of FDC-P1 cells. FDC-PI cells were grown to a density of about $1\times10^6$ cells/ml in 24 well tissue culture plates. Exponentially growing 1 ml individual cultures were then treated with varying concentrations of calmodulin antagonist, N-(6-aminohexyl)-5-chloro-1-naphthalenesulfonamide hydrochloride (W-7) or chlorine-deficient analogue of W-7, N-(6-aminohexyl)-1-naphthalenesulfonamide hydrochloride (W-5) (both W-7 and W-5 were purchased from Seikagaku Kogyo Co., Tokyo, Japan). Control cultures received equal amounts of phosphate-buffered saline, which was used for diluting the drugs W-7 and W-5. Fifteen minutes following the drug treatment, cells were incubated with 5 μCi/ml of $^3$H-thymidine (purchased from ICN Biomedicals, Inc., Costa Mesa, Calif.) for 60 minutes. Incorporation of $^3$H-thymidine into acid-precipitable material was terminated by adding trichloroacetic acid (TCA) to a final concentration of 10% to each culture. Cultures were incubated on ice for 15 minutes and the precipitate formed was recovered by centrifugation at 10K rpm for 10 minutes in Sorvall RC-5B centrifuge using SM-24 rotor. Precipitate was dissolved in 0.5 ml of 0.4M NaOH and reprecipitated by adding TCA to a final concentration of 10% and incubating on ice for 15 minutes. Each sample was diluted 5 fold with ice cold $H_2O$ and the precipitate was once again recovered by centrifugation. Precipitate was then dissolved in 0.5 ml of 0.4M NaOH, and 0.1 ml aliquots were counted for radioactivity in 5 ml "Ready Protein" scintillation cocktail (Beckman).

Preparation of lysates. Cells grown in suspension or following trypsinization of those grown in monolayers were collected by centrifugation and washed once with buffer A (35 mM hepes (7.4), 150 mm Sucrose, 80 mM KCl, 5 mM potassium phosphate (7.4), 5 mM $MgCl_2$, 0.05 mM $CaCl_2$, 8 mM dithiothreitol, and 1 mM phenylmethyl-sulfonyl fluoride). Cells were then suspended in buffer A at a density of $5\times10^7$ cells/ml and homogenized in a top-driven Wheaton homogenizer until about 90% of the cells can be stained with trypan blue. The supernatant obtained by centrifugation at 700× and 4° C. for 10 minutes was treated as cytoplasmic fraction. The pellet containing nuclear fraction was suspended in buffer A, to the same density as cells, and sonicated by using Branson Sonifier 250, equipped with micro-tip, at an output setting of 1.5–2 and a duty cycle of 20% for 30 to 40 pulses. The nuclear homogenate was then cleared by centrifugation at 5K rpm and 4° C. for 10 minutes in RC-5B Sorvall centrifuge equipped with SS-34 rotor, and the supernatant was treated as the nuclear fraction.

Synchronization of FDC-P1 cells in culture. Logarithmically growing FDC-P1 cells, that were adapted to grow in DMEM supplemented with 10% FCS, 25% WEHI-3 cm, 100 units/ml penicillin, 100 μg/ml streptomycin, were washed once in isoleucine-deficient DMEM and suspended in isoleucine-deficient DMEM containing 10% dialyzed FCS (purchased from Sigma Chemical Co.), 25% dialyzed WEHI-3 cm (dialyzed against phosphate-buffered saline), 100 units/ml penicillin, and 100 µg/ml streptomycin, and incubated at 37° C. in a humidified incubator with 5% $CO_2$ for 32 to 36 hours. These cells were then harvested by centrifugation and suspended in complete medium containing 10% FCS and 25% WEHI-3 cm or IL-3 (100 units/ml) in place of WEHI-3 cm. Synchronous progression of cells from G1 to S phase was then monitored by examining $^3$H-thymidine incorporation into DNA, at regular intervals after releasing from isoleucine block, as described above.

Deprivation and re-addition of hemopoietic growth factors to cells. Cells were deprived of growth factors by harvesting and washing them once in medium containing FCS but no WEHI-3 cm or cytokines. Cells were then incubated in cytokine-free medium containing 10% FCS for 16–18 hours. These cells essentially stop proliferating as determined by $^3$H-thymidine uptake and cell count measurements (data not shown). Specific cytokines or the WEHI-3 cm containing cytokines were then added back at appropriate concentrations and incubated for 6 to 12 hours. At 12 hours following the addition of cytokines cells begin to incorporate $^3$H-thymidine into their DNA.

Identification of calmodulin-binding proteins (CaM-BPs). Unless otherwise noted, 40 to 50 µg of protein samples of either cytoplasmic or nuclear fractions were subjected to polyacrylamide gel electrophoresis under denaturing conditions as described by Laemmli using mini-gel apparatus (Biorad). Proteins resolved on 10% polyacrylamide gels were then transferred to nitrocellulose filters at 200 mA for 1–2 hours in a Hopfer Scientific "transphor electrophoresis" unit. CaM-BPs on the filters were identified by employing biotinylated-CaM (purchased from Biomedical Technologies, Inc., Stoughton, Mass.) and alkaline phosphatase conjugated avidin (purchased from Boehringer Mannheim Biochemicals, Indianapolis, Ind.) as described by Billingsley et al. The specificity of binding of CaM to the proteins transferred to nitrocellulose filters in this assay was determined by its dependence on $Ca^{2+}$, and by its sensitivity to CaM antagonist W-7 as described by Billingsley et al. Prestained molecular weight markers (purchased from Bethesda Research Laboratories, Md.) were used to identify relative molecular weights of CaM-BPs detected on the filters.

Thymidine kinase assay. FDC-P1 cell lysates prepared at regular intervals after releasing from isoleucine block were assayed for thymidine kinase activity essentially as described elsewhere.

Protein estimation. Protein content in individual fractions was determined by the method of Lowry et al.

RESULTS

Effect of W-7 and W-5 on $^3$H-thymidine incorporation into DNA of FDC-P1 cells. We observed that the factor-dependent proliferation of myeloid FDC-P1 cells is inhibited by N-(6-aminohexyl)-5-chloro-1-naphthalenesulfonamide hydrochloride (W-7), a CaM antagonist, as determined by $^3$H-thymidine incorporation into DNA (FIG. 1). The effect of W-7 seems to be specifically due to the inactivation of CaM, since the chlorine deficient analogue of W-7, N-(6-aminohexyl)-1-naphthalenesulfonamide hydrochloride (W-5), a weaker antagonist for CaM is less effective in causing similar effects (FIG. 1). This observation is consistent with the report that IL-3, GM-CSF, or G-CSF-stimulated colony formation of myeloid progenitor cells is sensitive to CaM antagonists and, therefore, CaM may play a role in proliferation of myeloid progenitor cells.

Figure 2:
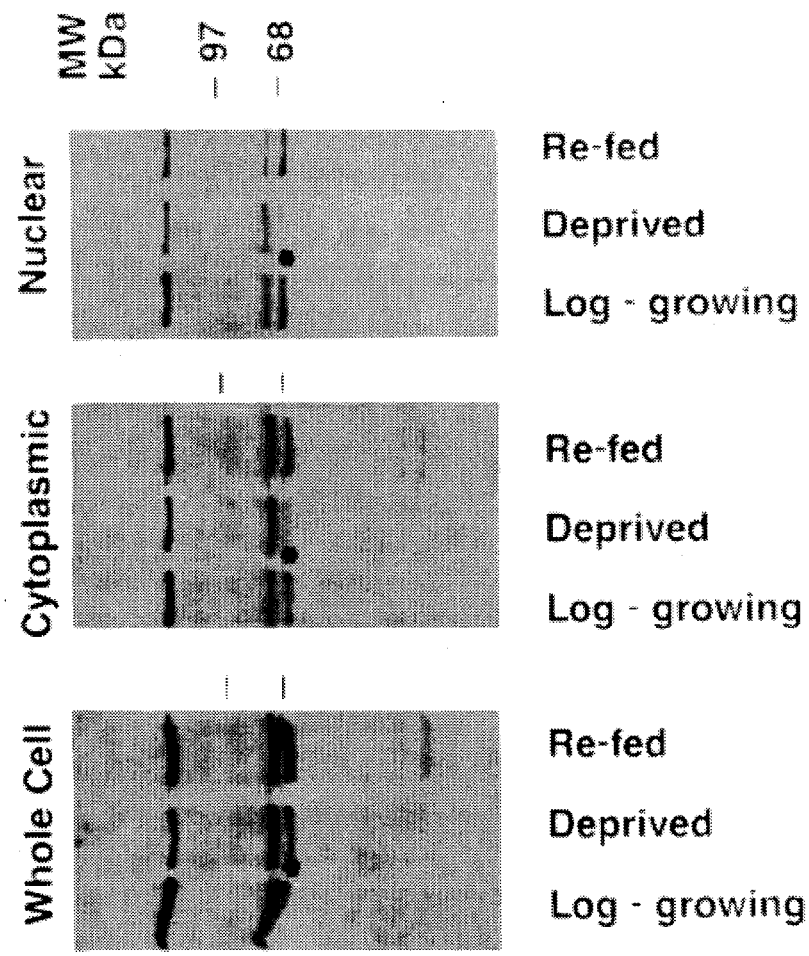
FIG. 2 illustrates the effect of the deprivation and re-addition of WEHI-3 cm on calmodulin-binding proteins in whole cell, cytoplastic and nucleolysates of FDC-P1 cells.

Effect of growth factor deprivation on calmodulin-binding proteins (CaM-BPs) in FDC-P1 cells. In order to evaluate further the causal relationship between CaM inactivation and prevention of cell proliferation, we examined intracellular distribution of specific CaM-BPs in response to proliferation associated cytokines in FDC-P1 cells. We found that when FDC-P1 cells were deprived of growth factors, by eliminating WEHI-3 conditioned medium (cm) in the culture medium, they stopped growing (data not shown), and concomitantly there was a significant decrease in a specific CaM-BP of about 68 kDa in the whole cell lysate (FIG. 2). Such a decrease was more evident in the cytoplasmic and nuclear fractions of the cells deprived of WEHI-3 cm (FIG. 2). In whole cell lysates, as compared to cytoplasmic and nuclear fractions, there was relatively more protein representing membrane and other cellular components. The decrease of the 68 kDa CaM-BP in the absence of WEHI-3 cm is intriguing, particularly, when one considers that this decrease was independent of the factors in the fetal calf serum to which the cells were constantly exposed even during WEHI-3 cm deprivation. Furthermore, when the cells were re-exposed to WEHI-3 cm, there was an almost complete restoration of 68 kDa CaM-BP levels in whole cell lysate, and a corresponding increase in both the cytoplasmic and the nuclear fractions, reaching levels observed with exponentially growing cultures (FIG. 2) and the cells subsequently began to proliferate (data not shown).

Figure 3A:
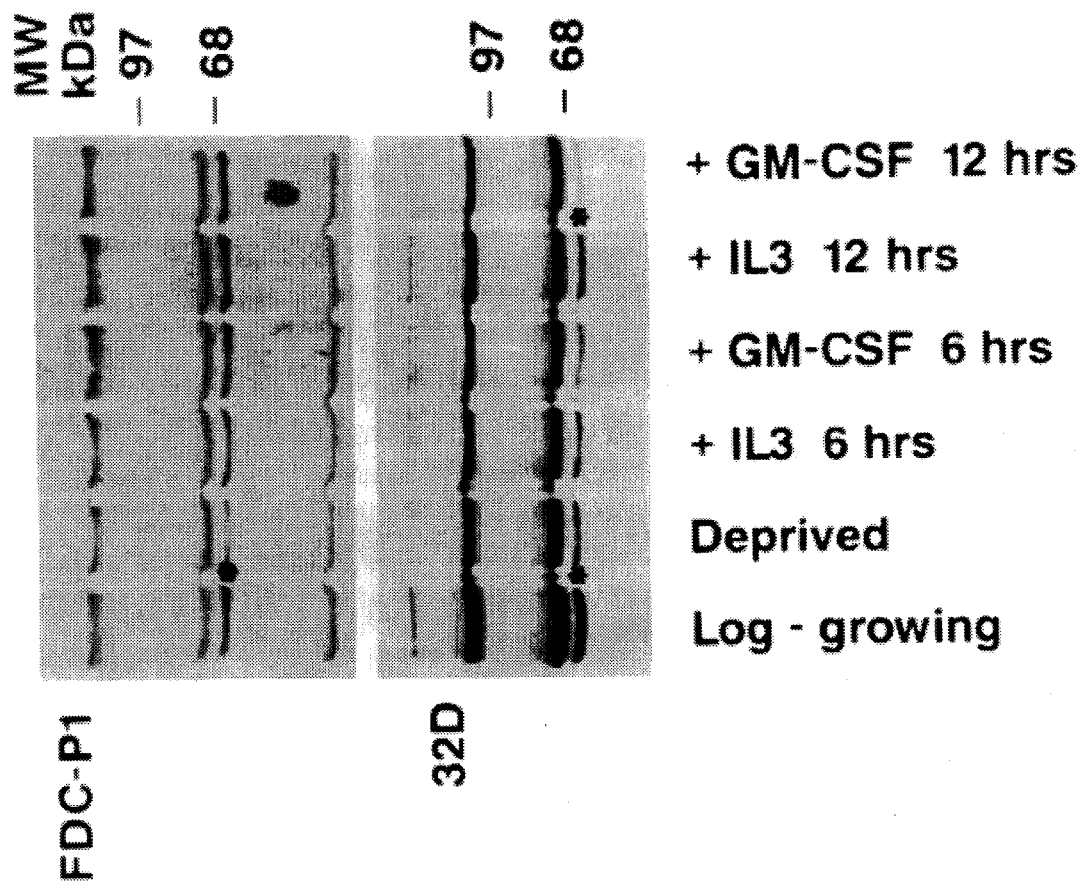
Figure 3B:
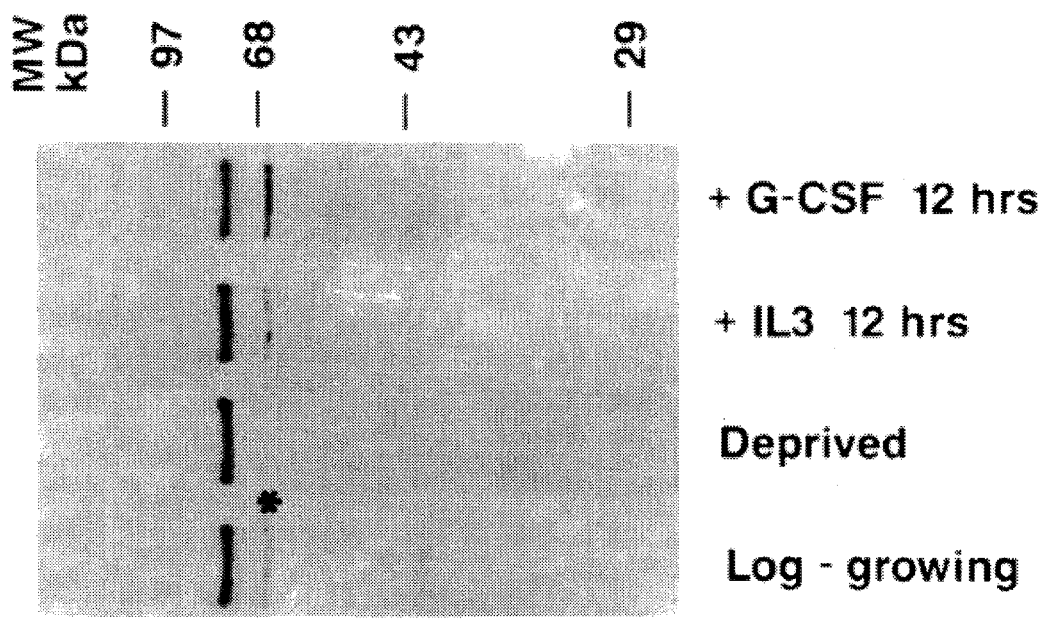

Effect of specific growth factors on the restoration of the 68 kDa CaM-BP in the cells deprived of growth factors. Restoration of 68 kDa CaM-BP levels by WEHI-3 cm in FDC-P1 cells is probably due to the presence of IL-3 since this is the major cytokine present in WEHI-3 cm to which FDC-P1 cells respond with proliferation. This was further explored by refeeding WEHI-3 cm deprived cells with IL-3 or GM-MF in place of WEHI-3 cm. As shown in FIG. 3A, these cytokines, individually, could substitute for WEHI-3 cm in restoring 68 kDa CaM-BP in the nuclear fraction of FDC-P1 cells. Thus, from these observations it seems that the restoration of the 68 kDa CaM-BP may occur, particularly, in response to cytokines with proliferative potential on specific factor-dependent hemolymphopoietic cells. This concept is supported by examining 32D, NFS-60, and T1165 cells. When 32D cells were growth factor deprived there was a decrease in the nuclear 68 kDa CaM-BP (FIG. 3A), which could be reversed only in the presence of IL-3 (which supports the proliferation of 32D cells) but not in the presence of GM-CSF (which does not support the growth of 32D cells). Actually, in the presence of GM-CSF, the nuclear 68 kDa CaM-BP continued to decrease with time (FIG. 3A). Similar changes in the nuclear 68 kDa CaM-BP were seen in NFS-60 cells when deprived for WEHI-3 cm and when re-exposed to specific growth factors (IL-3 and G-CSF) that induce their proliferation (FIG. 3B). IL-6-dependent T1165 cells also exhibited changes in cytoplasmic as well as the nuclear 68 kDa CaM-BP in response to growth factor deprivation and readdition (FIG. 3C). From these studies it is evident that the modulation of nuclear and cytoplasmic the 68 kDa CaM-BP in hemopoietic cells is highly dependent on the exposure of the cells to growth factors, acting through the hemopoietin receptor family.

Figure 4A:
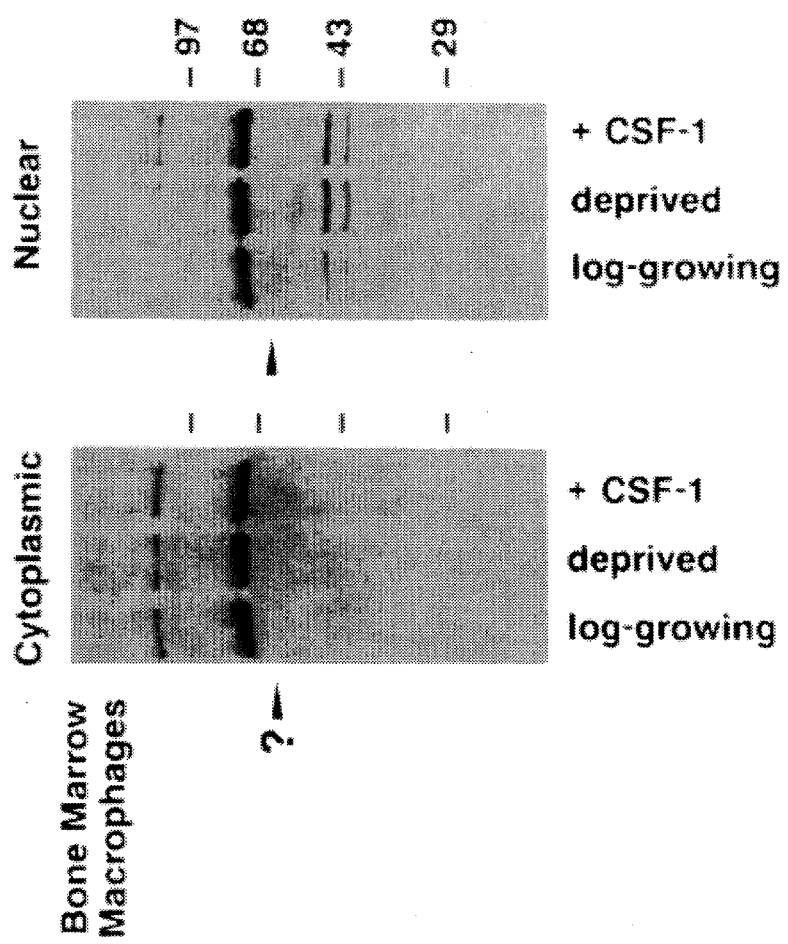
FIGS. 4A and 4B illustrate the effect of CSF-1 on CaM-BPs in bone marrow macrophages and BAC-1 cells.
Figure 4B:
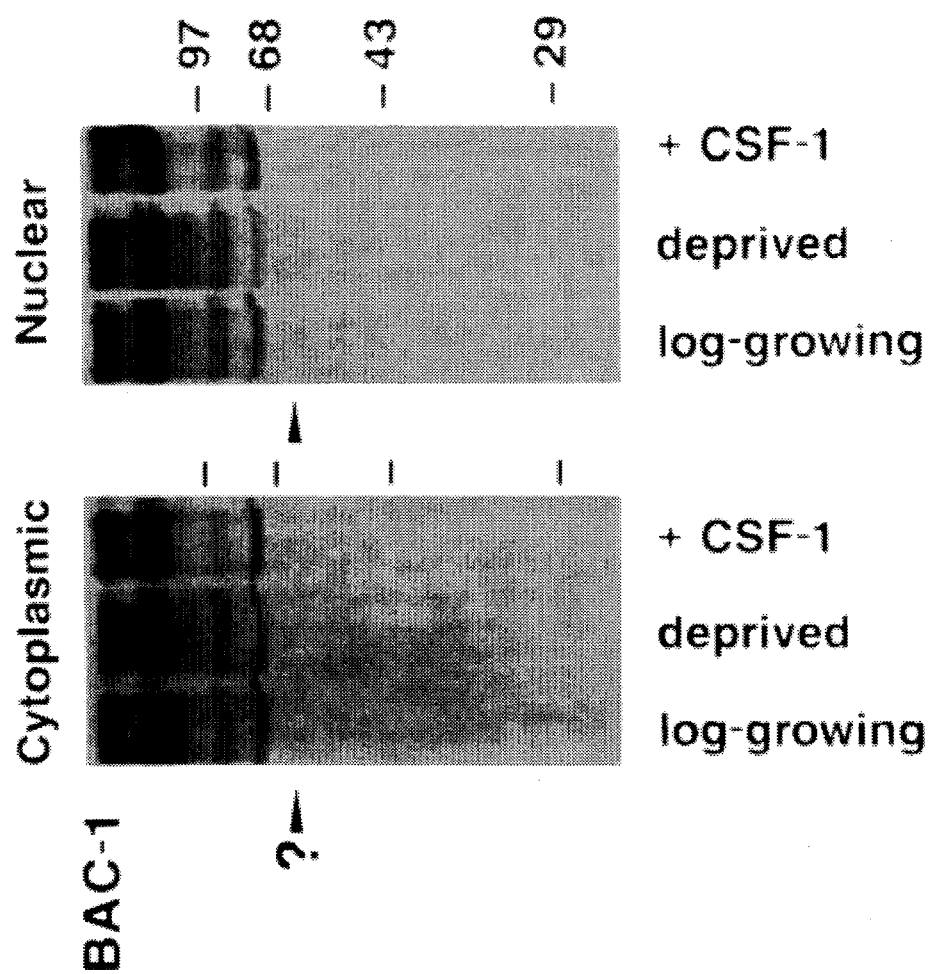

In our investigations to test universality of the relationship between growth factor induced proliferation and the stability of the 68 kDa CaM-BP in hemopoietic cells, we examined CSF-1-dependent bone marrow macrophages and BAC-1 cells. In contrast to IL-3-, IL-6, G-CSF-, or GM-CSF-dependent hemopoietic cells, 68 kDa CaM-BP could not be detected in cytoplasmic or nuclear fractions of bone marrow macrophages (FIG. 4A) or in BAC-1 cell (FIG. 4B). Thus, CSF-1 induced proliferation may involve 68 kDa CaM-BP-independent pathways.

Figure 5A:
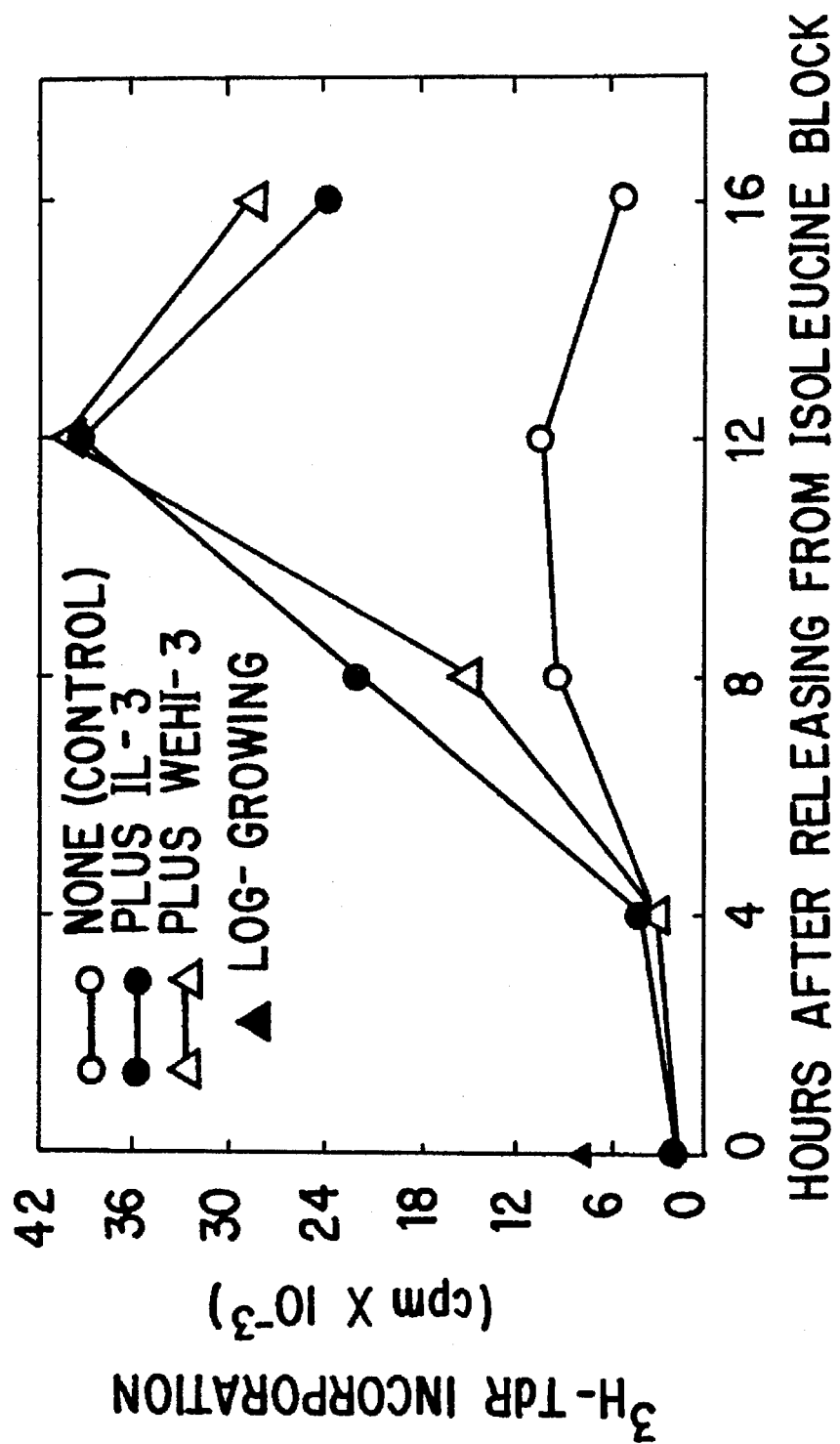
FIGS. 5A and 5B illustrate synchronization in WEHI-3 cm- or IL-3-dependent progression of FDC-P1 cells from G1 to S phase.
Figure 5B:
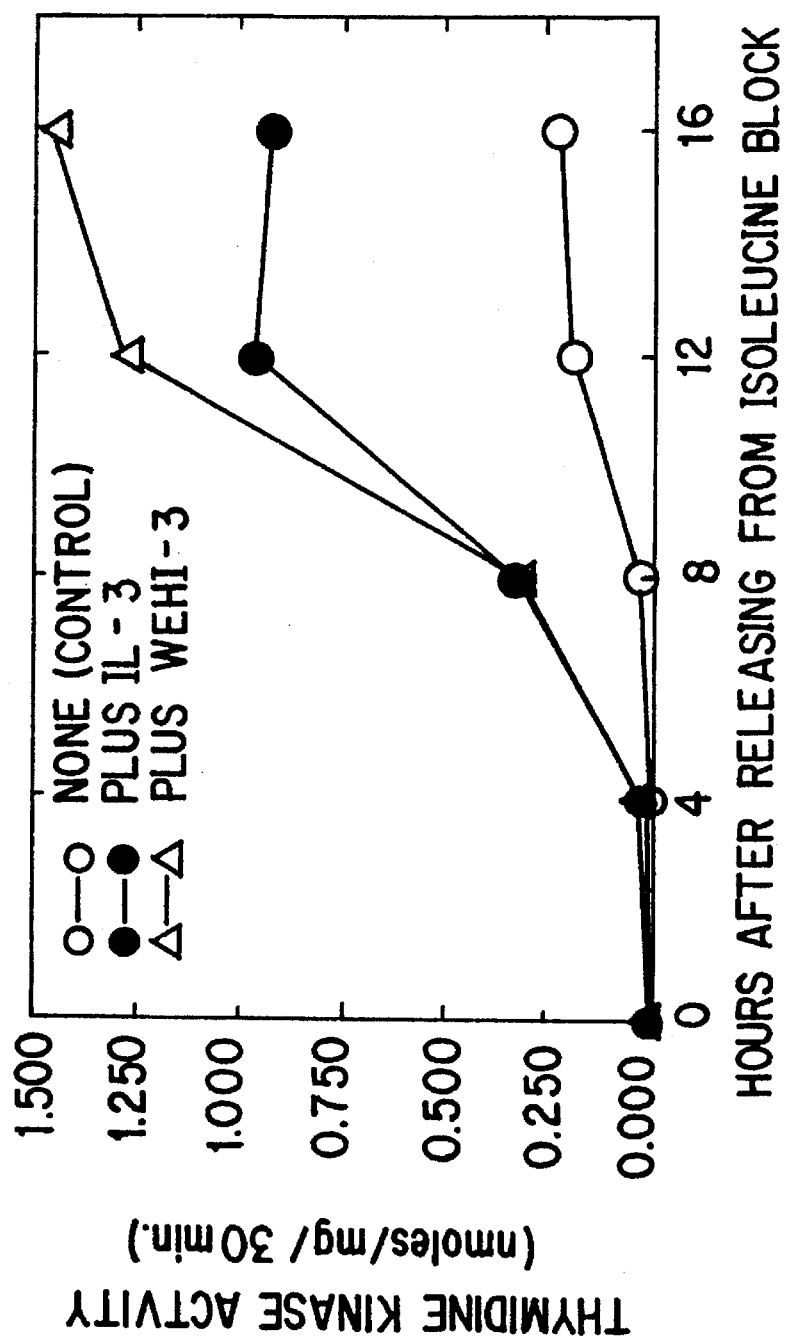

Synchronization of FDC-P1 cells. In order to understand the significance of the nuclear and cytoplasmic localization of the 68 kDa CaM-BP in growth factor-dependent proliferation of hemopoietic cells, we have developed a cell synchronization method in which the relationship between the intracellular distribution of the 68 kDa CaM-BP and the induction of S phase could be evaluated. As shown in FIG. 5A, FDC-P1 cells synchronized by isoleucine starvation method could progress from G1 to S phase only in the presence of WEHI-3 cm or IL-3. However, in the absence of the growth factors (i.e., WEHI-3 cm or IL-3), but in the presence of medium with 10% fetal bovine serum alone, cells did not progress through the cell cycle from G1 to S phase (FIG. 5A), even though more than 90% of the cells were viable at all times as determined by Trypan Blue exclusion method. Additional evidence for the synchronous progression of FDC-P1 cells from G1 to S phase in the presence of IL-3 or WEHI-3 cm, but not in their absence, is provided by the expression of thymidine kinase activity (FIG. 5B), a late-G1 marker.

Figure 6A:
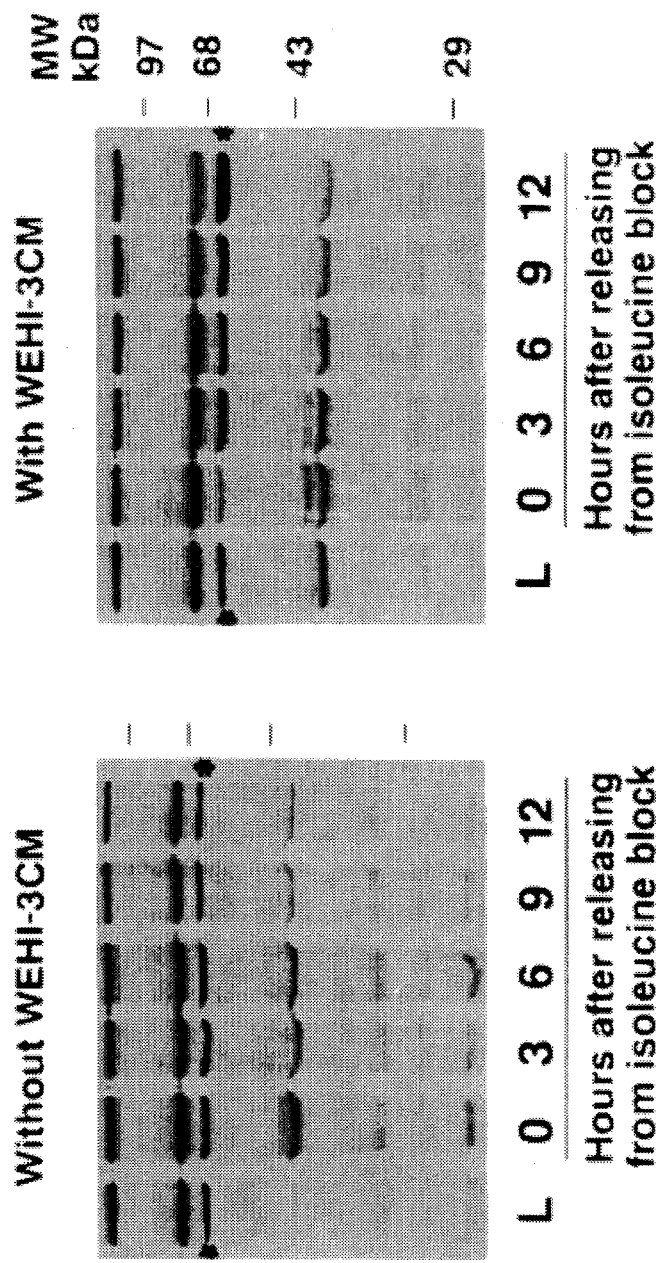
FIGS. 6A through 6D illustrate changes in 68 kDa CaM-BP as FDC-P1 cells progress synchronously from G1 to S phase.
Figure 6B:
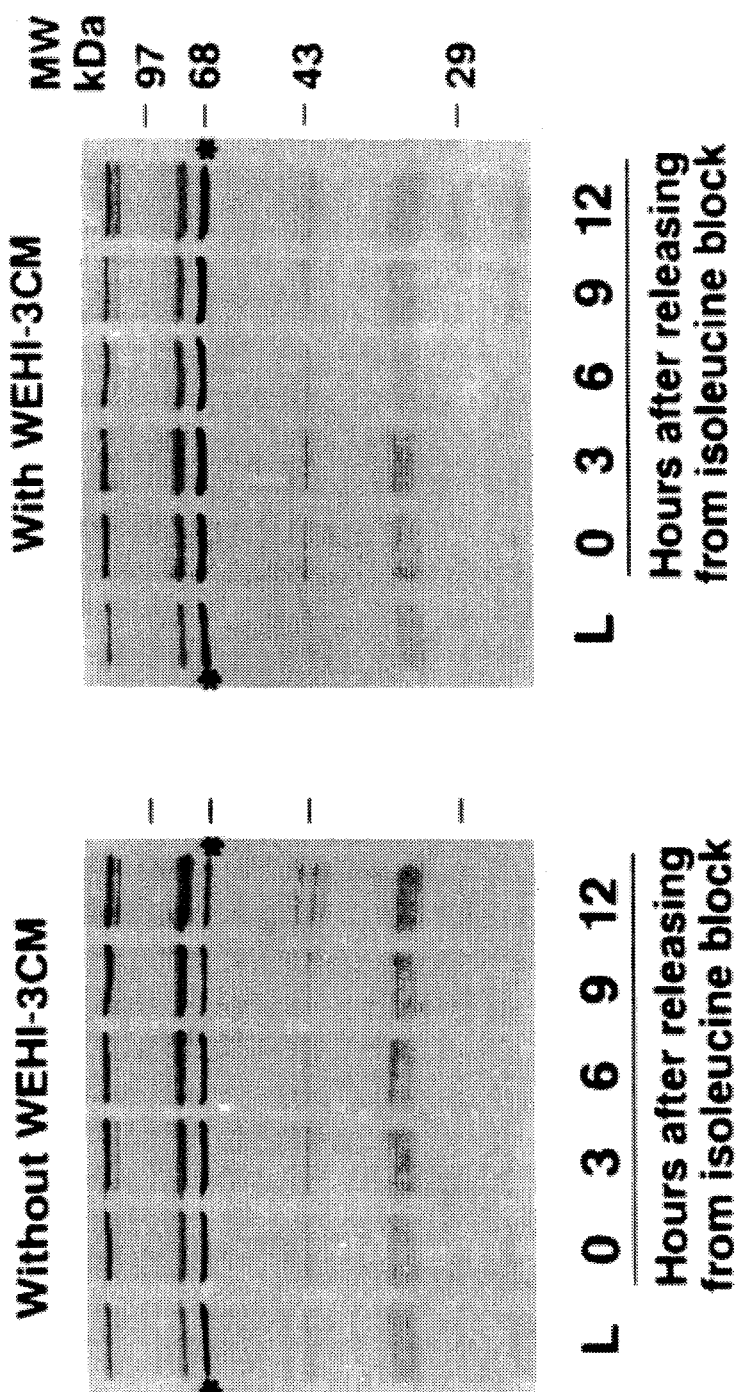
Figure 6C:
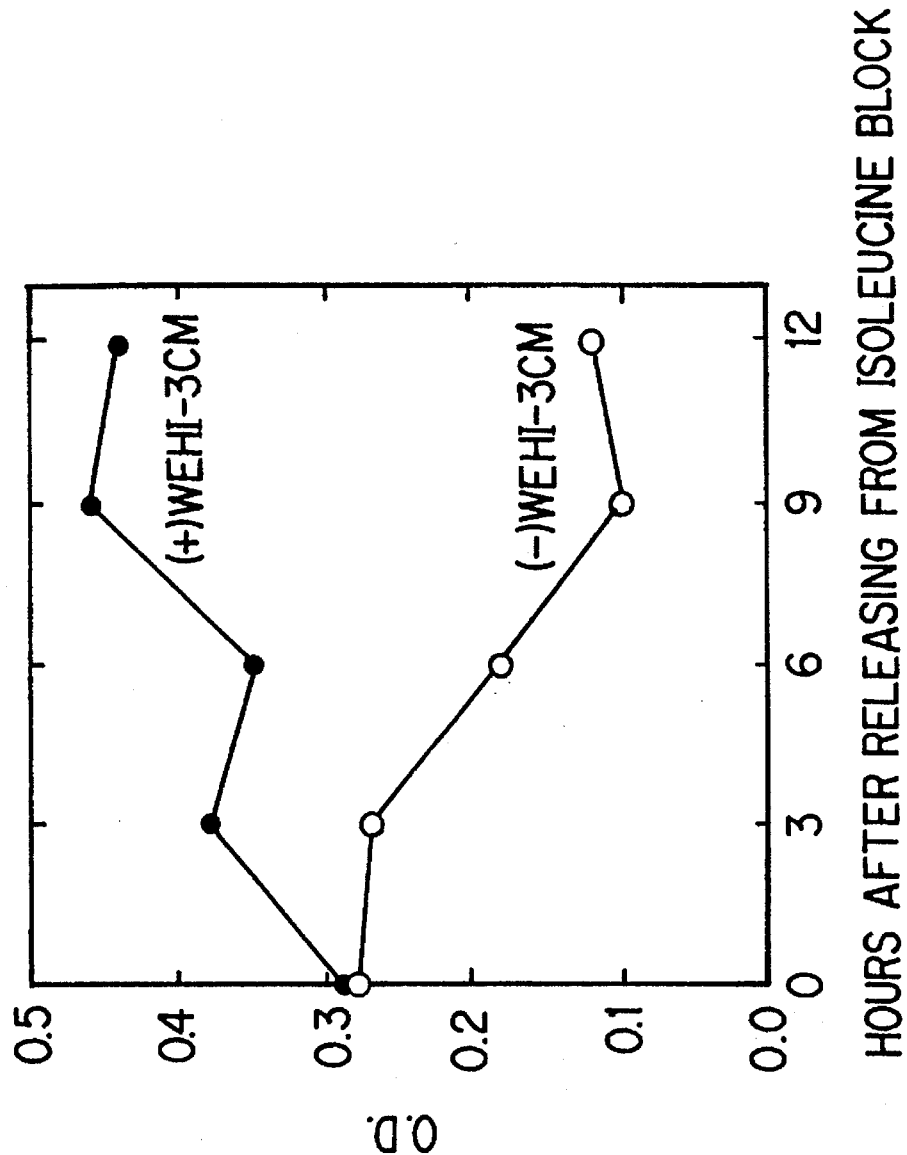
Figure 6D:
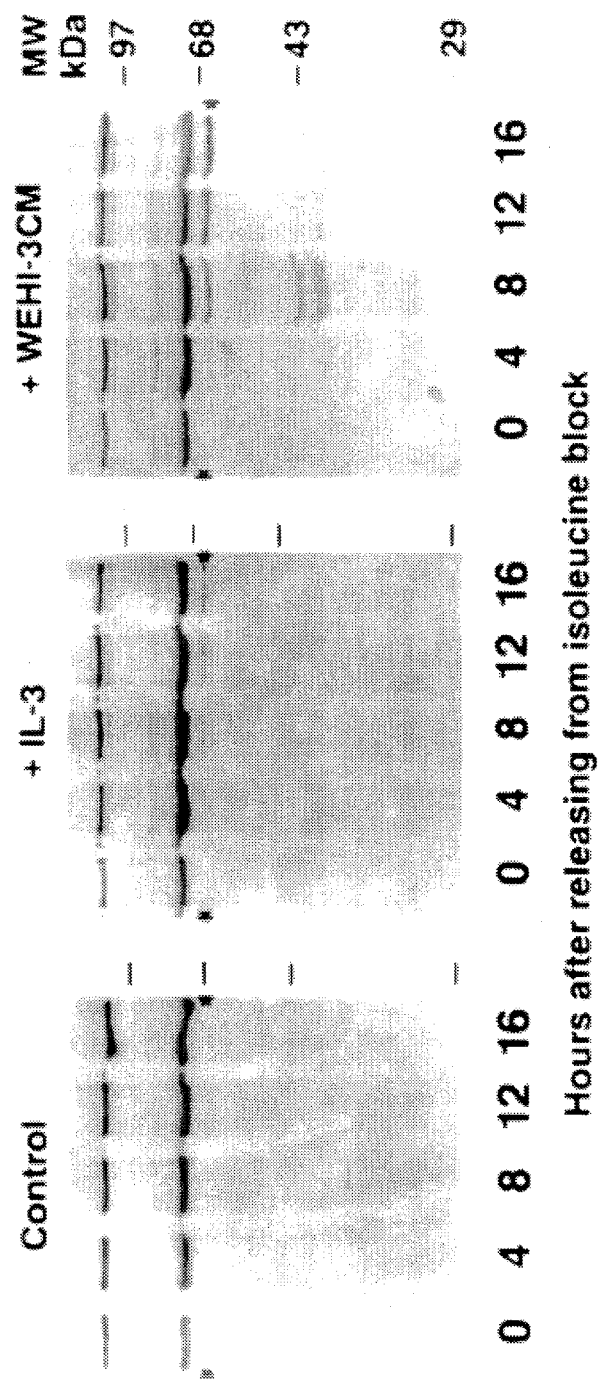

Intracellular distribution of CaM-BPs as FDC-P1 cells progress synchronously from G1 to S phase. An analysis of the CaM-BPs at regular intervals as cells progressed synchronously from G1 to S revealed that the nuclear levels of the 68 kDa CaM-BP is associated preferentially with the ability of cells to progress from G1 to S phase in response to growth factors. In the cells released from isoleucine block, while cytoplasmic 68 kDa CaM-BP remained relatively stable at all times following the removal of WEHI-3 cm, it increased 2–3 fold as cells progressed from G1 to S phase in the presence of WEHI-3 cm (FIG. 6A). In these cells, there was a gradual increase in nuclear 68 kDa CaM-BP corresponding to their ability to progress from G1 to S phase in the presence of WEHI-3 cm (FIG. 6B). However, in cells deprived of WEHI-3 cm, there was a significant decrease in nuclear 68 kDa CaM-BP, during a 12 hour period after releasing from isoleucine block (FIG. 6B). A dramatic difference in nuclear 68 kDa CaM-BP in the presence and the absence of WEHI-3 cm, particularly at the time (8 to 10 hours after releasing from isoleucine block) when the cells are scheduled to progress from G1 to S phase (FIG. 5A), is evident from the densitometric analysis of the 68 kDa CaM-BP band on original filters (FIG. 6C). A similar densitometric analysis of other two CaM-BPs (of about 75 and 120 kDa) did not exhibit any significant changes following the release from an isoleucine block that corresponded with the ability of cells to progress from G1 to S phase (data not shown). Once again, the recovery of the 68 kDa CaM-BP in the nuclei at the time when cells begin to progress from G1 to S phase was also observed in the presence of IL-3 alone, as well as in the presence of WEHI-3 cm (FIG. 6D). In this experiment, when smaller quantities of protein (20 μg, instead of 50 μg, per lane) were analyzed on the filters, the 68 kDa CaM-BP was hardly visible in the nuclear fraction at any time in the absence of the growth factors (FIG. 6D), and the cells failed to progress into S phase (FIG. 5A). These observations demonstrate that the nuclear location of the 68 kDa CaM-BP is associated preferentially with the ability of hemopoietic cells to progress from G1 to S phase.

The present data indicate that the growth factor-dependent induction and modulation of the 68 kDa CAM-BP may control the transition of hemopoietic cells from G1 to S phase. We have shown that the cytoplasmic nuclear levels of the 68 kDa CaM-BP are highly dependent on, and seems to be unique to, the growth factors with proliferation potential. Furthermore, the nuclear localization of this protein is temporally related to the ability of FDC-P1 cells to progress from G1 to S phase in synchronized cultures.

Hemolymphopoietic cell proliferation is highly sensitive to CaM antagonists, and is dependent on the availability of $Ca^{+2}$ containing culture medium. Accordingly we observed that $^3$H-thymidine incorporation into DNA of FDC-P1 cells is inhibited by the inactivation of intracellular CaM (FIG. 1). CaM is shown to be critically involved in proliferation of a variety of mammalian cells, particularly, at G1/S boundary. CaM levels are elevated 2 to 3 fold during late G1 period, and a direct correlation was observed between intracellular CaM levels and the ability of mammalian cells to replicate DNA. Furthermore, the stimulatory effect of $Ca^{+2}$ on DNA synthesis is blocked by CaM-antagonists, or -antibody. While these observations point to a pivotal role of CaM in cellular proliferation, its mechanism of action in inducing cell growth remains obscure.

In the present studies, we have identified a protein of about 68 kDa that binds specifically to CaM and whose stability and nuclear localization were dependent on the exposure of hemopoietic cells to growth factors. The binding specificity of CaM to this protein was detected by the requirement of $Ca^{+2}$ in CaM-binding assay, and the binding of CaM to the proteins on nitrocellulose filters was inhibited by CaM antagonist, W-7, as described by Billingsley et al. Among several CaM-BPs in cytoplasmic and nuclear fractions of hemopoietic cells identified by the CaM binding assay employed in the present studies, we observed that 68 kDa protein is the only CaM-BP that exhibited consistent and reproducible changes in response to the availability of growth factors in the culture medium. The growth factors, preferentially those with a potential to induce cellular proliferation, are involved in nuclear and cytoplasmic induction, and of the 68 kDa CaM-BP as exemplified by the observations that IL-3, but not GM-CSF, is capable of restoring the 68 kDa CaM-BP in 32D cells deprived of growth factors (FIG. 3A). In the presence of GM-CSF, which does not promote the proliferation of 32D cells, there was a continued depletion of the 68 kDa CAM-BP both in the nuclear (FIG. 3A), as well as cytoplasmic fractions. IL-3 and GM-CSF in FDC-P1 cells, IL-3 and G-CSF in NFS-60 cells, and IL-6 in T1165 cells, were able to restore 68 kDa CAM-BP in growth factor deprived cells in accordance with their abilities to induce cellular proliferation.

In a sharp contrast to the observations made with IL-3-, GM-CSF-, G-CSF-, and IL-6-dependent hemopoietic cells, CSF-1-dependent cells exhibited complete absence of the 68 kDa CaM-BP in their cytoplasmic and nuclear fractions. This is verified by examining two different cell systems, viz., bone marrow macrophages and BAC-1 cells (FIGS. 4A and 4B). However, it is not clear from our observations whether minor changes observed in other CaM-BPs, following deprivation or re-addition of CSF-1, could bear any significance in regulating proliferation of CSF-1-dependent cells. An absence of 68 kDa CaM-BP in CSF-1-dependent cells is intriguing particularly in the light of structural differences between CSF-1 receptor, c-fms proto-oncogene product, and the hemopoietin receptor family. Furthermore, while the CSF-1 receptor is a tyrosine kinase, IL-3, GM-CSF, G-CSF, and IL-6 receptors have no known kinase activity. Since CSF-1 and PDGF receptors are grouped together as tyrosine kinase receptors with structural similarities, it is possible that, like PDGF, CSF-1 in hemopoietic cells could serve as progression factor during early stages of G1 period. On the other hand, IL-3, GM-CSF, G-CSF, and IL-6 may serve as competence factors, as has been described for somatomedins. Thus, it is possible that 68 kDa CaM-BP dependent pathways in growth factor action may be unique to those that serve as competence factors. This is consistent with our earlier observation that the nuclear localization of the 68 kDa CaM-BP is associated with insulin-mediated onset of DNA replication in fibroblast cells.

The changes in intracellular protein(s) that are intimately involved in signal transduction following growth factor-receptor interaction are often indistinguishable from those that are occurring as a consequence of returning of the cells from a growth arrested state. By employing cell synchronization method, involving isoleucine starvation method to offset the cells in early G1 phase and then monitoring the ability of cells to progress into S phase in response to growth factors, we were able to distinguish changes in 68 kDa CaM-BP that are unique to growth factor-dependent progression of FDC-P1 cells from G1 to S phase (FIG. 6). In synchronized FDC-P1 cells, we observed a temporal relationship between the nuclear localization of the 68 kDa CaM-BP and $^3$H-thymidine incorporation into DNA. In addition, the 68 kDa CaM-BP could not be detected in nuclear fraction of the cells that were released from isoleucine block but were subsequently deprived for growth factors (FIG. 6C). These observations clearly demonstrate that the nuclear localization of the 68 kDa CAM-BP is intrinsic to the proliferative stimulation of hemopoietic cells by growth factors.

Our identification of 68 kDa CaM-BP as a mediator CaM action in cellular proliferation is consistent with the mechanisms by which CaM is known to regulate other metabolic processes. CaM, a ubiquitous protein, is known to control several metabolic processes in mammalian cells by its binding to specific regulatory proteins/enzymes. Similarly, $Ca^{+2}$/CaM, as second messengers in the action of growth factors, may regulate DNA synthesis by binding to the protein(s) associated with the enzymes of DNA replication. In this regard, it is interesting to note that specific CaM-BPs are tightly associated with purified DNA polymerase-α from a variety of mammalian cells. It is also observed that the 68 kDa CaM-BP is associated with the multienzyme complex, called replitase responsible for nuclear DNA replication in mammalian cells. A temporal interaction of the 68 kDa CaM-BP with the enzymes of DNA replication, as predicted from its nuclear localization in synchronized FDC-P1 cells (FIG. 6C), during cell cycle may possibly govern the assembly and/or structural stability of replitase complex that determines the catalytic activity of DNA synthesizing enzymes.

There are many proteins with 68 kDa molecular weight that are known to be regulated in response to proliferative stimulation. These proteins include $Na^+$,$H^+$ antiporter, p68 nuclear protein from HeLa cells, human p68 protein with RNA helicase activity, and cell cycle restriction protein. While each of these proteins has potential to serve the regulatory role in the control of cellular proliferation, it is not known whether any of them also bind to CaM to account for the 68 kDa CaM-BP identified in the present studies.

Altogether, our observations indicate that the proliferative signals generated by IL-3, IL-6, GM-CSF, and G-CSF in myeloid progenitor cells are transmitted to the nucleus via a specific 68 kDa CaM-BP. Furthermore, from earlier observations with insulin in fibroblast cells and from the present studies with four different factor-dependent myeloid cells, it seems that the signal transduction pathways leading to the onset of DNA replication by growth factors at G1/S boundary are being controlled by a common mechanism involving modulation of the 68 kDa CaM-BP in a variety of mammalian cells. Such a role for the 68 kDa CaM-BP may also attribute to a stringent requirement of $Ca^{+2}$ for the proliferation of hemolymphopoietic cells.

General Procedure for Isolating 68 kDa CaM-BP from FDC-P1 Cells

Generally, FDC-P1 cells at a density of about $5 \times 10^6$ cells/ml in buffer A (20 mM tris-HCl pH 7.4, 150 mM sucrose, 50 mM KCl, 0.2 µM $CaCl_2$, 4 mM $MgCl_2$, 1 mM PMSF) are homogenized and treated with a high salt concentration (0.5M KCl) to solubilize most of the nuclear 68 kDa CaM-BP.

The cell extract after it is clarified by centrifugation is applied to a sephacryl-S300 gel filtration column and developed with buffer B (buffer A without sucrose). The CaM-binding proteins in each fraction are identified by biotinylated-CaM binding assay.

Fractions containing 68 kDa CaM-BP from Sephacryl-S300 column are pooled and concentrated ten-fold by Amicon filtration and loaded on anion-exchange (SynChropak Ax-500) HPLC column equilibrated with buffer B. This column is then developed with a step gradient of 0.14M, 0.32M, and 0.5M KCl containing buffer B, and the fractions containing 68 KDa CaM-BP, eluted with 0.14M KCl (FIG. 5), are pooled. This pooled fraction are then dialyzed against buffer C (20 mM tris-HCl pH 7.4, 0.2 mM $CaCl_2$, 1 mM PMSF and 1 mM EDTA) and applied to Salmon sperm native DNA-cellulose column. The column, after a brief wash with buffer C, is developed with a linear gradient of 0 to 1.0M KCl. In our studies, we observed that fibroblast-derived 68 KDa CaM-BP is eluted at about 0.5 KCl by this procedure.

Since 68 kDa protein is the only CaM-BP in the DNA-cellulose fraction, CaM-Sepharose 4B is employed following DNA-cellulose chromatography. By introducing this step in the purification scheme, 68 kDa CaM-BP can be resolved from the remaining minor contaminating proteins in the DNA-cellulose fraction. Procedures for using CaM-Sepharose 4B, in purification of CaM-BP's, have been described by Sharma. In addition to CaM-Sepharose, based on our findings on the ability of the 68 kDa CaM-BP from FDC-P1 cells to bind to heparin or concanavalin A, heparin- and or concanavalin A-Sepharose chromatography may be employed.

While biotinylated-calmodulin-binding assay is the standard assay for the detection of 68 kDa CaM-BP during the entire course of its purification, where ever possible, the presence of the 68 kDa CaM-BP will be verified by assaying for its effect on the rate of $^3$H-dTTP incorporation into presence of the 68 kDa CaM-BP by assaying for its effect on the rate of $^3$H-dTTP incorporation into DNA in permeabilized cells and/or by CaM-dependent phosphodiesterase (PDE) inhibition assay as described by Speaker et al. However, because of the contamination of the 68 kDa CaM-BP containing fraction with DNA polymerase and PDE, neither of these two assays are suitable for the detection of the 68 kDa CaM-BP containing fractions during early steps of its purification, particularly during steps prior to SynChropak-HPLC. Therefore, it is desirable to rely upon detecting the 68 kDa CaM-BP fractions by CaM-binding assay as described by Billingsley et al, *Proc. Nat. Acad. Sci.*, U.S.A.

82, 7585–7589 1985 and Subramanyam et al, *J. Cell. Physiol.* 144, 423–428 1990.

Preparation of Antibodies

Generally, monoclonal and polyclonal antibodies to the present CaM-BP may be prepared by injection (i.e.)—(about 6) with 10 to 20 micrograms of purified 68 kDa CaM-BP in appropriate adjuvant and injecting two to three times more with the same quantities of the protein of about 10 day intervals. Ten to 15 days after the last injection, serum from each mouse is assessed for antibody production by enzyme-linked immunosorbent assay (ELISA). Mice that produce high titer of antibody are boosted (i.v.) one more time with 25 to 50 micrograms of protein and 4 days later, spleen cells from such mice are washed and fused with five sp 2/O-Ag 14 myeloma cells as described by the known method of Champan et al. See *J. Immunol.* 133:2488–2494 (1984).

More specifically, the standard mouse fusion protocol is modified from published procedures such as Oi, v.t. and Herzenberg, L. A. *Selected Methods in Cellular Immunology*, ed. B. B. Mishell and S. M. Shiigi, W. H. Freeman & Company, 1980, page 351).

More specifically spleen cells from an immunized mouse are washed once and in Iscove's MDM and mixed with washed sp 2/O-Ag 14 Myeloma cells (Schulman, et al. (1978), *Nature* 276:269) at a 5:1 ratio (splenocyte to myeloma). The cells are pelleted and the medium aspirated. Cell fusion is accomplished by the stepwise addition of 37% polyethylene glycol (PEG 1000, KOCH-light) over one minute.

PEG is then diluted dropwise with 10 ml Iscove's, MDM and the cells pelleted and gently washed once Iscove's MDM containing 15% selected fetal bovine serum, hypoxanthine (H) and thymidine (T). The cells are suspended in this HT medium, transferred to a petri dish and incubated at 37° C. in a humidified atmosphere of 5% $Co_2$/95% air for one hour. The cells are then resuspended in HT medium and plated into 96-well tissue culture plates (costar, Cambridge, Mass.) at a density of approximately $2-4\times10^5$ cell/well. The cultures are fed 24 hours later with HT medium containing aminopterin (HAT medium) and maintaining this medium for two weeks. Microscopic colonies usually appear within 7 to 10 days following the fusion and supernatents are screened for specific antibody production. Positive hybrids are cloned twice by limiting dilution, and frozen cell stocks are stored in liquid nitrogen cell banks. Monoclonal antibodies may also be routinely generated as either ascites, or as culture supernatants, in either fetal bovine serum-containing medium or in a defined medium (40 µ/ml total protein) which contains no serum.

Furthermore, the antibodies obtained in accordance with the present invention have high specificity to the 68 kDa CaM-BP.

The immunogenic response may be determined in mouse injected with 68 kDa CaM-BP by first bleeding the tails and determining the ability of serum to immune-precipitate 68 kDa CaM-BP from cytosolic and nuclear soluble fractions. Presence of the 68 kDa CaM-BP may be determined in immuno-precipitates by biotinylated-CaM-binding assay as described for cytoplasmic and nuclear fractions. In order to obtain hybridomas with high specificity to the 68 kDa CaM-BP, two or more stages of cloning are effected until a single-cell clone is obtained which is capable of producing monoclonal antibodies as described.

If the immune response to the antigen is not observed in mice or rats, because of its conserved nature in different murine species, the purified 68 kDa CaM-BP may be modified as described by Sacks et al, *Anal. Biochem.*, 194, 369 (1991).

Alternatively, polyclonal antibodies may be obtained by immunizing rabbit, sheep, goat or pig with purified 68 kDa CaM-BP from murine cells.

cDNA Cloning

Two independent approaches may be used to obtain a cDNA clone. One entails screening a small cDNA library with oligonucleotide probes and the other involves screening the cDNA library, in λ ZAP II) with antibody probes.

In order to synthesize oligonucleotides corresponding to the amino acid sequence of the 68 kDa CaM-BP, the amino acid sequence is obtained from the purified protein. Sequencing of the protein may be conducted as described by Matsudaira, 1987. For this procedure, about 50 pmoles of the purified protein is needed. Sequence information obtained from these studies is then used to design blots of mRNA. The protein sequence coded for by the least degenerate amino acid codons which is determined to specific for the 68 kDa CaM-BP is selected for probe desing. This is done using the DNA/Protein Sequence Analysis facilities available to the molecular biology user group at the University of Virginia Academic Computing Center. Both the sequence analysis of the purified protein and the synthesis of oligonucleotides are carried out with the help of the Protein and Nucleic Acid Research Facility at the University of Virginia. Oligonucleotides (15–20 nucleotides long), corresponding to all specific coding sequences for the sequenced portion of the 68 kDa CaM-BP are used to screen the FDC-P1 cDNA library.

A cDNA library may be constructed in the vector λZAPII from Stratagene, Inc. (La Jolla, Calif.) using FDC-P1 polyA+ mRNA. This library can be screened by either oligonucleotides or the control of the β-galactosidase promoter. λZAPII also has the benefits of an Ampicillin resistance gene for selection and easy excision/subcloning of cloned sequences into the plasmid pBlueScript. The cDNA may be constructed by the method of Gubler & Hoffman using random primers rather than oligo dT which generates longer, more full-length cDNA products.

Oligonucleotides designed as probes for 68 kDa CaM-BP may be used as probes on Northern blots of FDC-P1 mRNAs to determine probe fidelity and specificity. Those probes which appropriately hybridize to the message from 68 kDa CaM-BP may be used to recover cDNA clones with homologous pBlueScript. These cDNAs may be sequenced using the dideoxy sequencing method of Sanger et al and their relation to the 68 kDa CaM-BP protein sequence verified. These 68 kDa CaM-BP cDNAs are then available as probes to study 68 kDa-mRNA expression and gene regulation, as well as the relationship of these sequences to other genes.

An alternative scheme to recover a cDNA clone(s) utilizes polyclonal or monoclonal antibodies as probes. The FDC-P1 cDNA sequences may be expressed as bacterial fusion proteins in λZAPII. The antibodies should first be checked for their ability to immunoprecipitate 68 kKa CaM-BP from in vivo translated products of the RNA used for preparing cDNA library. This then enables the artisan to establish a) specificity of the antibody and b) presence of 68 kDa CaM-BP coding mRNA in this cDNA. The FDC-P1/λZAPII library may be screened initially with rabbit polyclonal antibody to 68 kDa CaM-BP (or a mouse monoclonal) which has been "preabsorbed" to *E. coli* proteins and confirmed to be negative for bacterial proteins and positive for the purified 68 kDa protein by Western blot. A lawn of *E. coli* XL1-Blue, in which cloned sequences can be expressed as fusion proteins by IPTG induction of the lacZ gene promoter, is incubated with an overlaying nitrocellulose filter (pretreated with 10 mM IPTG) for 4–8 hours then incubated with the primary antibody. The cDNA clones which bind antibody may be visualized by a secondary antibody, goat anti-mouse or anti-rabbit (depending on the source primary antibody), conjugated with alkaline phosphatase (developed with PicoBlue Immunoscreen kit, Stratagene) or with colloidal gold (Janssen Life Sciences, Aurogold conjugate).

Additionally, for more background information regarding the preparation and use of cDNA, reference may be made to U.S. Pat. Nos. 4,394,443 and 4,556,643 both of which patents are incorporated herein in their entirety.

Also, antisense constructs may be made as described in U.S. Pat. No. 4,999,290, also incorporated herein in the entirety.

Finally, in accordance with the present invention the 68 kDa CaM-BP has been determined to have the following characteristics.

Physical properties—68 kDa CaM-BP

The ability of this protein to bind to CaM in CaM-binding assay is stable at 4° C. for several days. Raising the temperatures to 50° C. for 5 minutes decreased its CaM-binding activity dramatically. CaM-binding activity of the protein is stable in a pH range of 6.5 to 8.5. A pH above or below this range diminished the detection of this protein by CaM-binding assay.

68 kDa CaM-BP from nuclear and cytosolic fraction of FDC-P1 cells is precipitated with 35% ammonium sulfate. On sephacryl S-200 gel filtration it eluted around 400 kDa molecular weight. This is observed irrespective of whether 68 kDa CaM-BP was extracted by ammonium sulfate precipitation prior to its application to S-200 column or nuclear lysate applied directly to S-200 column without ammonium sulfate treatment. This protein is eluted from a CaM-agarose affinity column with 10 mM EGTA-containing buffer. On anion-exchange HPLC it is eluted with 180–200 mM KCl.

In accordance with the present invention, the monoclonal or polyclonal antibodies are used in a concentration which is dependent upon the affinity of the antibody for the protein antigen. This is well within the skill of the artisan to make this determination as needed.

Having described the present invention, it will be apparent to one of ordinary skill in the art that many changes and modifications may be made without departing from the spirit and the scope of the present invention.

What is claimed and desired to be secured by United States Letters Patent is:

1. A calmodulin-binding protein having a molecular weight of 68 kDa as determined by gel electrophoresis under denaturing conditions on a 10% polyacrylamide gel, obtained from cytoplasmic or nuclear eukaryotic cell fractions, which is induced in hemopoietic factor-dependent cell lines by at least one cytokine selected from the group consisting of granulocyte-macrophage colony stimulating factor, granulocyte colony stimulating factor, interleukin-3 and interleukin-6.

2. A monoclonal antibody raised against the protein of claim 1, which is specifically reactive therewith.

3. The 68 kDa calmodulin-binding protein of claim 1, which binds to heparin or concanavalin A.

4. The calmodulin-binding protein of claim 1, which is obtained by:
   a) homogenizing FDC-P1 cells and treating the homogenized cells with a salt solution, thereby solubilizing substantially all nuclear calmodulin-binding protein, to obtain a cell extract;
   b) clarifying the cell extract by centrifugation, and developing the clarified extract on a gel filtration column;
   c) pooling fractions containing said calmodulin-binding protein from the column and concentrating the fractions and loading the concentrated fractions on an anion-exchange column and developing the column with a step gradient, and pooling fractions containing said calmodulin-binding protein;
   d) dialyzing the pooled fractions against buffer and applying the same to a DNA-cellulose column, and eluting said calmodulin-binding protein from the DNA-cellulose fraction.

5. The 68 kDa calmodulin-binding protein of claim 4, wherein said salt concentration in step a) is 0.5M KCl.

6. The 68 kDa calmodulin-binding protein of claim 4, wherein in step b, the gel filtration column is a sephacryl-5300 gel filtration column.

7. The 68 kDa calmodulin-binding protein of claim 4, wherein the step gradient comprises 0.14M, 0.32M and 0.5M KCl containing buffer.

8. The 68 kDa calmodulin-binding protein of claim 4, wherein in step d) the 68 kDa protein is eluted at about 0.5 KCl.

9. The 68 kDa calmodulin-binding protein of claim 4, which is the only CaM-BP in the DNA-cellulose fraction.

10. The calmodulin-binding protein of claim 4, obtained by a process which further comprises the steps of incubating said cells in a cytokine-free medium for 16–18 hours, then incubating said cells in a medium containing a cytokine selected from the group consisting of granulocyte-macrophage colony stimulating factor, granulocyte colony stimulating factor, interleukin-3 and interleukin-6 for 6–12 hours, prior to said homogenizing.

11. The calmodulin-binding protein of claim 1, in which the calmodulin-binding activity decreases after 5 minutes at a temperature of 50° C.

12. The calmodulin-binding protein of claim 11, in which the calmodulin-binding activity is stable in a pH range of from 6.5 to 8.5.

13. The calmodulin-binding protein of claim 1, which is precipitated with 35% ammonium sulfate.

14. The calmodulin-binding protein of claim 1, exhibiting a molecular weight of around 400 kDa on Sephacryl S-200 gel filtration.

15. The calmodulin-binding protein of claim 14, which elutes from calmodulin-agarose affinity column with 10 mM EGTA-containing buffer.

16. The calmodulin-binding protein of claim 15, which elutes from anion-exchange HPLC with 100–200 mM KCl.

17. The calmodulin-binding protein of claim 1, isolated from FDC-P1 cells.

* * * * *